(12) United States Patent
Jing

(10) Patent No.: US 10,888,495 B2
(45) Date of Patent: Jan. 12, 2021

(54) SCRAPING PLATE

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventor: Yangkun Jing, Beijing (CN)

(73) Assignees: BOE TECHNOLOGY GROUP CO., LTD., Beijing (CN); HEFEI BOE OPTOELECTRONICS TECHNOLOGY CO., LTD., Anhui (CN)

( * ) Notice: Subject to any disclaimer, the term of this patent is extended or adjusted under 35 U.S.C. 154(b) by 498 days.

(21) Appl. No.: 15/578,469

(22) PCT Filed: Jul. 7, 2017

(86) PCT No.: PCT/CN2017/092173
§ 371 (c)(1),
(2) Date: Nov. 30, 2017

(87) PCT Pub. No.: WO2018/040743
PCT Pub. Date: Mar. 8, 2018

(65) Prior Publication Data
US 2018/0303707 A1     Oct. 25, 2018

(30) Foreign Application Priority Data

Aug. 31, 2016   (CN) .......................... 2016 1 0794617

(51) Int. Cl.
*A61H 39/06*     (2006.01)
*A61F 7/00*      (2006.01)
(Continued)

(52) U.S. Cl.
CPC ............... *A61H 39/06* (2013.01); *A61F 7/00* (2013.01); *A61F 7/007* (2013.01); *A61H 7/00* (2013.01);
(Continued)

(58) Field of Classification Search
CPC .... A61B 2090/064; A61H 39/06; A61H 7/00; A61H 2201/5082; A61H 2201/5002;
(Continued)

(56) References Cited

U.S. PATENT DOCUMENTS

2008/0125682 A1*  5/2008  Bonneyrat ............. A61H 7/003
                                                        601/112
2014/0088351 A1*  3/2014  Murison  ............. F04B 11/0008
                                                         600/38
(Continued)

FOREIGN PATENT DOCUMENTS

CN       201591724 U    9/2010
CN       202490154 U    10/2012
(Continued)

OTHER PUBLICATIONS

CN 205234897U—English Translation.*
(Continued)

*Primary Examiner* — Quang D Thanh

(57) ABSTRACT

A scraping plate is provided. The scraping plate includes a main body, a storage chamber for storing a liquid medicine and an electric heater for heating the liquid medicine. One end of the main body is provided with a scraping blade, and the other end opposite to the scraping blade is provided with a grip portion. Both the storage chamber and the electric heater are provided inside the main body. A surface of the scraping blade is provided with at least one liquid medicine outlet, wherein each liquid medicine outlet is communicated with the storage chamber.

10 Claims, 2 Drawing Sheets

(51) Int. Cl.
*A61H 7/00* (2006.01)
*A61M 37/00* (2006.01)
*A61B 90/00* (2016.01)
*A61F 7/02* (2006.01)

(52) U.S. Cl.
CPC ....... *A61M 37/00* (2013.01); *A61B 2090/064* (2016.02); *A61F 2007/0052* (2013.01); *A61F 2007/0059* (2013.01); *A61F 2007/0072* (2013.01); *A61F 2007/0093* (2013.01); *A61F 2007/0095* (2013.01); *A61F 2007/0261* (2013.01); *A61H 2201/0207* (2013.01); *A61H 2201/5002* (2013.01); *A61H 2201/5028* (2013.01); *A61H 2201/5071* (2013.01); *A61H 2201/5082* (2013.01)

(58) Field of Classification Search
CPC .... A61H 2201/5028; A61H 2201/0207; A61H 2201/5071; A61H 7/003; A61H 2201/0153; A61H 2201/105; A61F 7/007; A61F 7/00; A61F 2007/0095; A61F 2007/0052; A61F 2007/0093; A61F 2007/0261; A61F 2007/0059; A61F 2007/0072; A61F 2007/0087; A61M 37/00; A61M 2037/0007
See application file for complete search history.

(56) References Cited

U.S. PATENT DOCUMENTS

2015/0165182 A1* 6/2015 Pratt .................... A61M 3/022
604/290
2017/0105870 A1* 4/2017 Yazdani ............... A41D 13/005

FOREIGN PATENT DOCUMENTS

| CN | 203970842 U | 12/2014 |
|---|---|---|
| CN | 204521476 U | 8/2015 |
| CN | 205234897 U | 5/2016 |
| CN | 106236535 A | 12/2016 |
| EP | 0673635 A1 | 9/1995 |
| TW | M345604 U | 12/2008 |

OTHER PUBLICATIONS

International Search Report and Written Opinion dated Jun. 25, 2017; PCT/CN2017/092173.
The First Chinese Office Action dated Jan. 10, 2018; Appln. No. 2016610794617.4.

* cited by examiner

SCRAPING PLATE

TECHNICAL FIELD

The present disclosure relates to a technical field of medical care, and more particularly, discloses a scraping plate.

BACKGROUND

Scraping is performing repeated scratching and rubbing on skin surface through a special scraping (GUA SHA) device and scraping method, with a certain medium dipped, so that dark red bleeding points appear in local skin, etc., so as to achieve effects of invigorating blood circulation and easing from acute filthy disease. An existing scraping plate does not have functions of moxibustion and transdermal administration.

SUMMARY

Embodiments of the present disclosure provide a scraping plate, the scraping plate has functions of moxibustion and transdermal administration, and is capable of lubricating skin through a liquid medicine while scraping is performed, so as to maintain the skin at a comfortable temperature, which facilitates medicine absorption and achieves good scraping effect.

One of embodiments of the present disclosure provides a scraping plate comprising: a main body, one end of the main body being provided with a scraping blade, and the other end opposite to the scraping blade being provided with a grip portion; a storage chamber for storing a liquid medicine and an electric heater for heating the liquid medicine, both the storage chamber and the electric heater being provided inside the main body; at least one liquid medicine outlet, provided on a surface of the scraping blade, wherein each liquid medicine outlet is communicated with the storage chamber.

In an embodiment, each liquid medicine outlet is communicated with the storage chamber through a connecting tube.

In an embodiment, the electric heater is provided on an inner bottom of the storage chamber.

In an embodiment, the electric heater is provided on an outer peripheral surface of the connecting tube.

In an embodiment, the scrapping plate further comprises a switch provided on the main body and configured for turning on or turning off of the electric heater.

In an embodiment, the scrapping plate further comprises a valve and a controller, wherein the valve is mounted on the connecting tube for controlling open and close of an internal channel of the connecting tube, and the valve is in signal communication with the controller.

In an embodiment, the scrapping plate further comprises a pressure detector, wherein the pressure detector is provided inside the grip portion and at least a portion of the pressure detector is exposed out of the grip portion for detecting a pressure of the grip portion, and transmitting the detected pressure to the controller; the controller is provided inside the main body, and is in signal communication with the pressure detector; the controller is configured for comparing the received pressure with a preset pressure, if the pressure is equal to or larger than the preset pressure, the controller controls the valve to open, so that the internal channel of the connecting tube is communicated with the storage chamber.

In an embodiment, the scrapping plate further comprises a temperature detector provided inside the scraping blade and a temperature controller provided inside the main body, wherein the temperature detector is configured for detecting a temperature of the liquid medicine in the liquid medicine outlet, and transmitting detected temperature to the temperature controller; the temperature controller is in signal communication with both the temperature detector and the electric heater, and configured for controlling the electric heater according to the detected temperature transmitted by the temperature detector, so that the temperature of the liquid medicine in the storage chamber is equal to or lower than a preset temperature.

In an embodiment, the main body is provided with a liquid medicine injection port communicated with the storage chamber and a seal cover for sealing and covering the liquid medicine injection port.

In an embodiment, the electric heater is a microwave heater, an infrared heater, or a resistance heater.

In an embodiment, a liner bushing made of a flexible material is embedded into each liquid medicine outlet, the liner bushing protrudes from a corresponding liquid medicine outlet to out of the scraping blade.

In an embodiment, the flexible material is carbon nanotube rubber.

In an embodiment, the connecting tube comprises a main tube and a branch tube, one end of the main tube is communicated with the storage chamber, and the other end is communicated with the branch tube.

In an embodiment, a valve is provided on the main tube to control communication of the main tube.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Embodiments of the present disclosure provide a scraping plate, the scraping plate has functions of moxibustion and transdermal administration, and is capable of lubricating skin through a liquid medicine while scraping is performed, so as to maintain the skin at a comfortable temperature, which facilitates medicine absorption and achieves good scraping effect.

Figure 1:
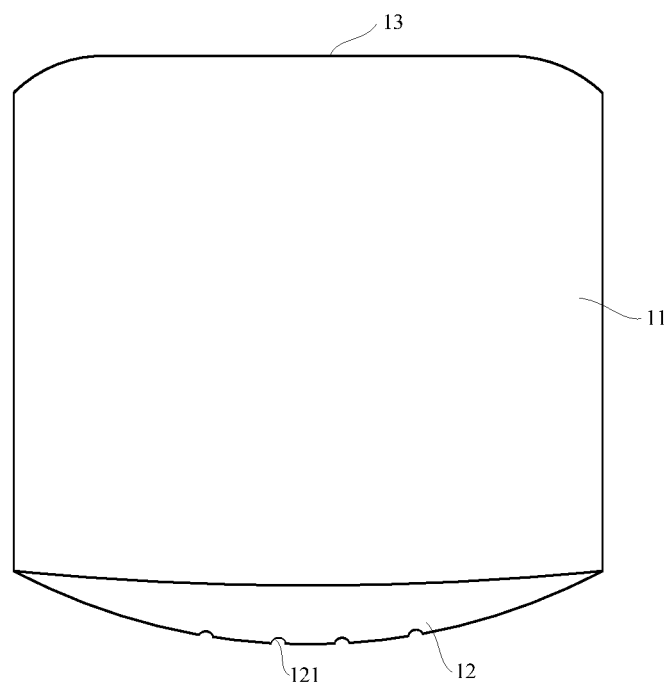
FIG. 1 is a schematic diagram of a scraping plate provided by an embodiment of the present disclosure.
Figure 2:
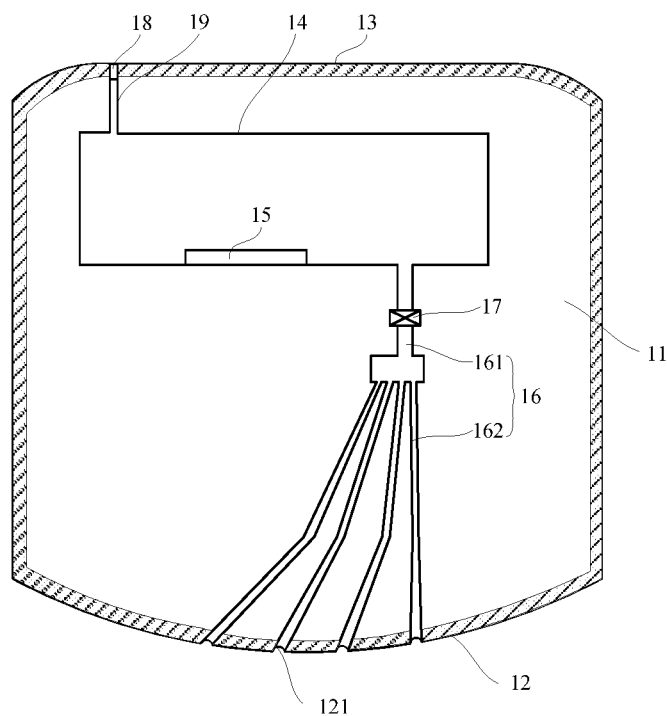
FIG. 2 is an internal schematic diagram of a scraping plate provided by an embodiment of the present disclosure.

With reference to FIG. 1 and FIG. 2, the scraping plate provided by the embodiment of the present disclosure, comprises: a main body 11, one end of the main body 11 being provided with a scraping blade 12, and the other end opposite to the scraping blade 12 being provided with a grip portion 13. The scraping plate further comprises a storage chamber 14 for storing liquid medicine and an electric heater 15 for heating the liquid medicine. Both the storage chamber 14 and the electric heater 15 are provided inside the main body 11. At least one liquid medicine outlet 121a is provided on the surface of the scraping blade 12, and each liquid medicine outlet 121 is communicated with the storage chamber 14.

As illustrated in FIG. 1 and FIG. 2, the scraping plate is provided with the scraping blade 12 at one end of the main body, and is provided with the grip portion 13 at the other end of the main body opposite to the scraping blade 12. In addition, the scraping plate is provided with the storage chamber 14 inside the main body 11, and provided with the electric heater 15 at an inner bottom of the storage chamber 14, and provided with a plurality of liquid medicine outlets 121, for example, four liquid medicine outlets 121 as illustrated in FIG. 2, on the surface of the scraping blade 12. While the scraping is performed on the skin with the above-described scraping plate, the liquid medicine filled in the storage chamber 14 is heated by the electric heater 15, and the liquid medicine within the storage chamber 14 flows out through the liquid medicine outlet 121 of the surface of the scraping blade 12. The liquid medicine has an increased temperature before flowing out because it has been heated by the electric heater 15. In this way, when the scraping is performed on the skin with the scraping blade 12, the heated liquid medicine in the storage chamber 14 flows out through the liquid medicine outlet 121 with movement of the scraping plate, and then be applied on the surface of the skin. On one hand, the heated liquid medicine can lubricate the skin and prevent the skin from being damaged by the repeated rubbing of the scraping plate; on the other hand, the heated liquid medicine can increase the temperature of the surface of the skin and perform moxibustion on the skin, which results in dilatation in skin pores and subcutaneous blood vessels in contact with the liquid medicine, and facilitating the liquid medicine to enter the skin. Then, the heated blood in the subcutaneous blood vessels can accelerate blood circulation. Therefore, at the same time of performing the scraping with the above-described scraping plate, it is not only capable of lubricating and heating the skin, so as to maintain the skin at a comfortable temperature, but also capable of performing administration and moxibustion through the skin, making the skin pores and subcutaneous blood vessels dilate with the heated liquid medicine, so as to increases the scraping effect and promote drug absorption.

Therefore, the scraping plate has functions of moxibustion and transdermal administration, and is capable of lubricating the skin with the liquid medicine at a same time when scraping is performed, so as to maintain the skin at a comfortable temperature, which facilitates drug absorption and has good scraping effect.

In at least some of embodiments, each liquid medicine outlet 121 is communicated with the storage chamber 14 through a connecting tube 16.

As illustrated in FIG. 2, each liquid medicine outlet 121 is communicated with the storage chamber 14 through the connecting tube 16. The connecting tube 16 comprises a main tube 161 and four branch tubes 162, one end of the main tube 161 is communicated with the storage chamber 14, and the other end is respectively communicated with four branch tubes 162. A valve 17 is provided on the main tube 161 to control the communication between the main tube 161 and the storage chamber 14, and to further control the communication between the storage chamber 14 and the liquid medicine outlets 121, so as to control whether or not the liquid medicine is applied on the surface of the skin while the scraping is performed.

The above-described respective branch tubes 162 may be capillaries, portions of the capillaries close to the scraping blade 12 are coiled within the main body, the scraping blade 12 is heated through the heated liquid medicine flowing through the capillary, so that the scraping blade 12 can be in contact with the skin under a comfortable temperature.

Depending on different positions where the electric heater 15 is provided, the scraping plate may have several implementations below:

In one example, as illustrated in FIG. 2, the electric heater 15 is provided at the inner bottom of the storage chamber 14.

In case that the electric heater 15 is provided at the inner bottom of the storage chamber 14, the electric heater 15 directly heats the liquid medicine in the storage chamber 14. While the liquid medicine is being heated, a volume of the liquid medicine or air in the storage chamber 14 will expand, so that a pressure will be generated and the pressure will push the liquid medicine to flow out. Therefore, in present example, the pressure for pushing the liquid medicine is generated while the liquid medicine is being heated.

In another example, the electric heater 15 is provided on an outer peripheral surface of the connecting tube 16.

In case that the electric heater 15 is provided on the outer peripheral surface of the connecting tube 16, the electric heater 15 surrounds the outer surface of the connecting tube 16 and heats the liquid medicine flowing in the connecting tube 16 through the connecting tube 16.

In yet another example, the electric heaters 15 are provided on the inner bottom of the storage chamber 14 and the outer peripheral surface of the connecting tube 16.

In case that the electric heaters 15 are provided on both the inner bottom of the storage chamber 14 and the outer peripheral surface of the connecting tube 16, the scraping plate is capable of sufficiently heating the liquid medicine through the respective electric heaters 15 provided on both the inner bottom of the storage chamber 14 and the outer peripheral surface of the connecting tube 16, which facilitates precise control of the temperature of the liquid medicine, so that the temperature of the liquid medicine is quickly reached to the desired temperature.

In the above-described embodiments, the electric heater 15 may be a microwave heater, an infrared heater or a resistance heater, and may also be other types of heaters is capable of heating the liquid medicine.

In case that the electric heater 15 is the microwave heater or the infrared heater, the electric heater 15 is provided outside the storage chamber 14 so as to heat the liquid medicine, and may prevent the electric heater 15 from contaminating the liquid medicine.

In case that the electric heater 15 is the infrared heater, the infrared heater may perform infrared therapy on the human body while heating the liquid medicine; infrared rays generated by the infrared heater may be applied to a site for therapy through clothes, and may also passes through the skin, so as to directly generate a heat effect on a muscle and subcutaneous tissue, which facilitates accelerating blood material circulation, increasing metabolism, reducing pain, promoting muscle relaxation, and resulting in a massage effect.

Therefore, when the electric heater 15 is the infrared heater, it is not only capable of performing scraping on the skin with the scraping plate, but also capable of performing physiotherapy on the human body through an emitted infrared ray, to generate a true multifunctional therapeutic effect.

In case that the electric heater 15 is the resistance heater, the resistance heater comprises positive and negative electrodes, and further comprises an electric heating wire or a positive temperature coefficient (PTC) thermistor, both ends of the electric heating wire or the PTC thermistor are respectively connected with the positive and negative electrodes, so that the electric heating wire or the PTC thermistor generate heat to heat the liquid medicine.

In at least some of embodiments, in order to facilitate turning on or turning off the electric heater 15, the above-described scraping plate further comprises a switch 20 provided on the main body 11 and configured for turning on or off the electric heater 12. The switch 20 may be provided on the surface of the main body, and the switch 20 is electrically connected with the electric heater 15, to turn on the electric heater 15 when it is necessary to heat the liquid medicine, and to turn off the electric heater 15 when it is not necessary to stop heating the liquid medicine, so that the scraping plate can be controlled easily.

Figure 4:
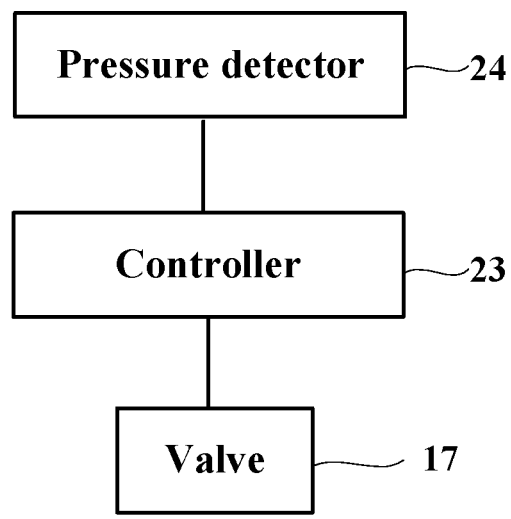
FIG. 4 is a principle diagram of a valve of a scraping plate provided by an embodiment of the present disclosure.

In at least some of embodiments, as illustrated in FIG. 4, the scraping plate further comprises a valve 17, a pressure detector 24 and a controller 23.

The valve 17 is mounted on the connecting tube 16 for controlling open and close of an internal channel of the connecting tube 16, and the valve 16 is in signal communication with the controller 23.

The pressure detector 24 is provided inside the grip portion 13 and has at least a portion thereof exposed out of the grip portion 13, for detecting a pressure of the grip portion 13, and transmitting the detected pressure to the controller 23.

The controller 23 is provided inside the main body 11, and is in signal communication with the pressure detector 24.

The controller 23 compares the received pressure with a preset pressure, if the pressure is equal to or larger than the preset pressure, the controller 23 opens the valve 17 to open, so that the internal channel of the connecting tube 16 is communicated with the storage chamber 14.

Therefore, in a process of performing scraping with the above-described scraping plate, a pressure applied to the grip portion 13 by a user is detected by the pressure detector 24 in the grip portion 13, and the detected pressure is compared with the preset pressure. If the detected pressure is larger than the preset pressure, it is determined that the scraping plate is being configured for scraping, and the valve 17 is controlled to open through the controller 23, to allow the liquid medicine in the storage chamber 14 to flow toward the skin surface through the valve 17, the connection tube 16 and the liquid medicine outlet 121, which lubricates the skin with the liquid medicine, and at a same time, administrates the medicine through the skin.

Therefore, open and close of the valve 17 is controlled by the pressure detector 24 and the controller 23, which can accurately control supply of the liquid medicine, avoid waste of the liquid medicine, increase effective utilization ratio of the liquid medicine, and further reduce medication cost of a patient. In at least some of embodiments, the scraping plate may comprise a controller 23 and a valve 17, without a pressure detector 24. The valve 17 is, for example, an electromagnetic valve.

Figure 3:
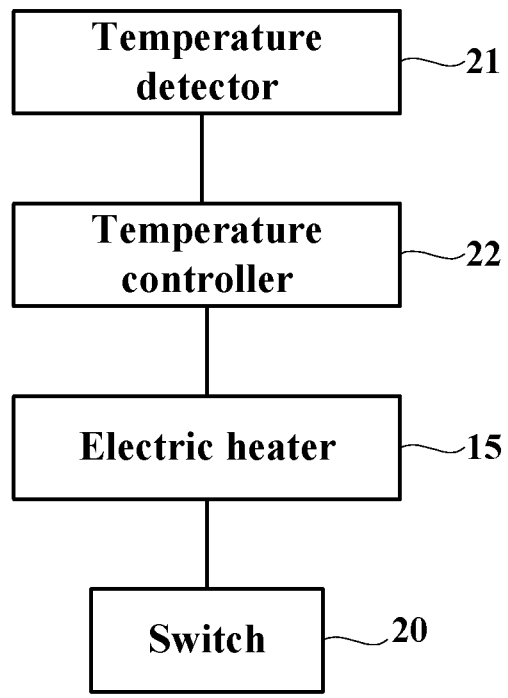
FIG. 3 is a principle diagram of an electric heater of a scraping plate provided by an embodiment of the present disclosure.

In at least some of embodiments, as illustrated in FIG. 3, the above-described scraping plate further comprises a temperature detector 21 provided inside the scraping blade 12 and a temperature controller 22 provided inside the main body 11.

The temperature detector 21 is configured for detecting a temperature of the liquid medicine in the liquid medicine outlet 121, and transmitting the detected temperature to the temperature controller 22.

The temperature controller 22 is in signal communication with both the temperature detector 21 and the electric heater 15, and controls the electric heater 15 according to the temperature transmitted by the temperature detector 21, so that the temperature of the liquid medicine in the storage chamber 14 is not smaller than the preset temperature.

In above-described scraping plate of the embodiment, the temperature detector 21 is configured for detecting the temperature of the liquid medicine in the liquid medicine outlet 121 and the temperature controller 22 is configured for controlling the electric heater 15. The temperature detector 21 transmits the detected temperature to the temperature controller 22, and the temperature controller 22 controls the electric heater 15, so as to control the temperature of the liquid medicine within reasonable working range. As a result, the scraping effect and transdermal administration effect can be increased, and the skin can be prevented from being scalded caused by the high temperature of the liquid medicine, moreover, the energy is saved.

In order to facilitate detecting the temperature of the liquid medicine in the liquid medicine outlet 121 provided in the scraping blade 12, the temperature detector 21 may be a temperature sensor, and may also be other detectors capable of detecting the temperature of the liquid medicine.

In order to increase applicability of the scraping plate with respect to different patients, as illustrated in FIG. 2, the main body 11 is provided with a liquid medicine injection port communicated with the storage chamber 14 and a seal cover 18 for sealing and covering the liquid medicine injection port.

Because the main body of the scraping plate is provided with the liquid medicine injection port and the seal cover 18, and the liquid medicine injection port is communicated with the storage chamber 14 through a catheter 19, an injector may be provided for injecting the liquid medicine to the storage chamber 14 through the liquid medicine injection port. In case that the liquid medicine in the storage chamber 14 is used up, new liquid medicine may be injected through the liquid medicine injection port, or liquid medicine with change in different recipes according to the condition of the patient may be injected through the liquid medicine injection port, so as to perform target therapy on the patient. Because the liquid medicine may be injected through the liquid medicine injection port, it is possible to reuse the scraping plate and inject special medical drugs for different patients, therefore, the utilization efficiency of the scraping plate can be increased, and the therapeutic effect on a disease can be increased.

The above-described seal cover 18 may be a rubber stopper, and may also be a plug screw with a sealing structure, and the like.

In order to increase the therapeutic effect of scraping, the scraping blade 12 is made of ceramic material, for example, ceramic material with micro-pores, so that the liquid medicine flows slowly out of micro-pores of the ceramic material, which allows the liquid medicine to be fully absorbed while lubricating the skin, increases the utilization ratio of the liquid medicine, and further increases the therapeutic effect. The scraping blade 12 may also be made of other materials, for example, Bian stone (i.e., stone used in acupuncture), an ox horn, or other materials suitable for the scraping plate.

Various regions of the skin may be scraped by the scraping plate. Due to different shapes in different regions of the skin, a liner bushing made of a flexible material is embedded into each liquid medicine outlet 121, in order to increase a matching degree between the scraping plate and different portions of the skin. The liner bushing is protruding from a corresponding liquid medicine outlet 121 out of the scraping blade 12, and the flexible material may be carbon nanotube rubber or silicon, or may be other types of flexible materials.

Tightness and adaptability between the scraping blade 12 and the skin may be increased by the liner bushing made of the flexible material, and the liner bushing may protect the skin from being damaged. The scraping plate may also be absorbed onto the skin surface through the liner bushing, and a pressure sensor device is provided, to control an adsorption pressure between the scraping plate and the skin, and to increase the therapeutic effect.

It should be noted that, the liquid medicine as mentioned in the embodiments of the present disclosure may be various liquid medicines capable of treating diseases, or an auxiliary product used in scraping, such as scraping oil, essential oil, and so on.

What is described above is related to the illustrative embodiments of the disclosure only and not limitative to the scope of the disclosure; the scopes of the disclosure are defined by the accompanying claims.

The present application claims priority of Chinese Patent Application No. 201610794617.4 filed on Aug. 31, 2016, the disclosure of which is incorporated herein by reference in its entirety as part of the present application.

The invention claimed is:

1. A scraping plate, comprising:
   a main body, one end of the main body being provided with a scraping blade, and an other end opposite to the scraping blade being provided with a grip portion;
   a storage chamber for storing a liquid medicine and an electric heater for heating the liquid medicine, both the storage chamber and the electric heater being provided inside the main body;
   at least one liquid medicine outlet, provided on a surface of the scraping blade, wherein each of the at least one liquid medicine outlet is communicated with the storage chamber through a connecting tube;
   a valve, mounted on the connecting tube for controlling open and close of an internal channel of the connecting tube;
   a controller, provided inside the main body, and is in signal communication with a pressure detector;
   the pressure detector, provided inside the grip portion and configured for detecting a pressure of the grip portion and transmitting the detected pressure to the controller, wherein the controller is configured for comparing the detected pressure with a preset pressure, when the detected pressure is equal to or larger than the preset pressure, the controller controls the valve to open, so that the internal channel of the connecting tube is communicated with the storage chamber.

2. The scraping plate according to claim 1, wherein the electric heater is provided on an inner bottom of the storage chamber.

3. The scraping plate according to claim 2, further comprising a switch configured for turning on or turning off of the electric heater.

4. The scraping plate according to claim 1, further comprising a temperature detector and a temperature controller, wherein the temperature detector is configured for detecting a temperature of the liquid medicine in the liquid medicine outlet, and transmitting detected temperature to the temperature controller;
   the temperature controller is in signal communication with both the temperature detector and the electric heater, and configured for controlling the electric heater according to the detected temperature transmitted by the temperature detector, so that the temperature of the liquid medicine in the storage chamber is equal to or lower than a preset temperature.

5. The scraping plate according to claim 1, wherein the main body is provided with a liquid medicine injection port communicated with the storage chamber and a seal cover for sealing and covering the liquid medicine injection port.

6. The scraping plate according to claim 1, wherein the electric heater is a microwave heater, an infrared heater, or a resistance heater.

7. The scraping plate according to claim 1, wherein a liner bushing made of a flexible material is embedded into each of the at least one liquid medicine outlet.

8. The scraping plate according to claim 7, wherein the flexible material is carbon nanotube rubber.

9. The scraping plate according to claim 1, wherein the connecting tube comprises a main tube and a branch tube, one end of the main tube is communicated with the storage chamber, and an other end of the main tube is communicated with the branch tube.

10. The scraping plate according to claim 9, wherein the valve is provided on the main tube to control communication of the main tube.

\* \* \* \* \*